United States Patent [19]
Cigaina

[11] Patent Number: 6,146,391
[45] Date of Patent: Nov. 14, 2000

[54] LAPAROSCOPIC FORCEPS

[75] Inventor: Valerio Cigaina, Treviso, Italy

[73] Assignee: Transneuronix, Inc., Mount Arlington, N.J.

[21] Appl. No.: 09/358,955

[22] Filed: Jul. 22, 1999

[30] Foreign Application Priority Data

Jul. 31, 1998 [IT] Italy .................................. MI98A1811

[51] Int. Cl.⁷ ................................................. A61B 17/00
[52] U.S. Cl. ............................................ 606/147; 606/205
[58] Field of Search ............................... 606/1, 138, 139, 606/147, 148, 205–210; 81/415

[56] References Cited

U.S. PATENT DOCUMENTS

| | | |
|---|---|---|
| 2,865,376 | 12/1958 | Pellier et al. . |
| 3,760,812 | 9/1973 | Timm et al. . |
| 4,444,207 | 4/1984 | Robicsek . |
| 4,475,560 | 10/1984 | Tarjan et al. . |
| 4,524,771 | 6/1985 | McGregor et al. . |
| 4,901,722 | 2/1990 | Noguchi . |
| 5,059,207 | 10/1991 | Shah . |
| 5,100,431 | 3/1992 | Buster et al. . |
| 5,217,471 | 6/1993 | Burkhart ................................. 606/205 |
| 5,222,962 | 6/1993 | Burkhart ................................. 606/207 |
| 5,242,458 | 9/1993 | Bendel et al. .......................... 606/205 |
| 5,423,872 | 6/1995 | Cigaina . |
| 5,423,876 | 6/1995 | Camps et al. . |
| 5,433,728 | 7/1995 | Kim . |
| 5,450,739 | 9/1995 | Bogart et al. . |
| 5,489,294 | 2/1996 | McVenes et al. . |
| 5,716,392 | 2/1998 | Bourgeois et al. . |

FOREIGN PATENT DOCUMENTS

| | | |
|---|---|---|
| 44 02 058 | 1/1994 | Germany . |
| WO 97/41921 | 11/1997 | WIPO . |

*Primary Examiner*—Michael Buiz
*Assistant Examiner*—William Lewis
*Attorney, Agent, or Firm*—Fitch, Even, Tabin & Flannery

[57] ABSTRACT

The present invention provides laparoscopic forceps which can grasp surgical and/or laparoscopic implements and automatically orient the surgical and/or laparoscopic implements to a predetermined orientation. The forceps are fashioned specifically for grasping the laparoscopic implement, and include grasping mechanisms located at one end of the shaft. The grasping mechanisms include orienting mechanisms effective to orient the implement in a predetermined orientation with respect to the forceps. In favorable embodiments, the grasping mechanism is effective to orient the implement automatically in the predetermined orientation, and consists of two jaws, each jaw including a flat surface and a recessed seat for receiving a portion of the implement defined on the flat surface of at least one of the jaws.

11 Claims, 3 Drawing Sheets

LAPAROSCOPIC FORCEPS

FIELD OF THE INVENTION

The present invention relates to a novel surgical tool, in particular, to laparoscopic forceps and methods of using such forceps. The forceps have grasping mechanisms specifically structured to grasp a surgical or other implement within the abdominal cavity during laparoscopic surgery and, upon grasping the implement, to automatically orient the implement to a predetermined orientation.

BACKGROUND OF THE INVENTION

A broad range of surgical techniques directed to the abdominal cavity are carried out using laparoscopic procedures. For example, in abdominal microsurgery or video laparoscopic surgery, a patient is placed under general anesthesia, and the abdomen is then inflated with a non-flammable inert gas such as $CO_2$ in order to transform the abdominal cavity from a virtual to an actual cavity. The provision of the cavity affords the laparoscopic surgeon the space within which laparoscopic tools and implements can be manipulated in order to carry out the laparoscopic procedure.

In order to accomplish the surgery or similar procedure, "trocars" are inserted that traverse the abdominal wall. A trocar is a rigid tube with gas-tight membranes that prevent the inflating gas from escaping from the abdomen during the procedure. Thereupon, a series of microimplements are inserted into the abdominal cavity through the trocars. These include, for example, a light source and video camera for visualizing the procedure, and other instruments for actually carrying out the surgical operation or similar procedure.

For a surgical operation of this kind, several trocars, frequently four or more, are normally used. Two of the trocars permit access to the abdomen by the video camera in order to monitor the movements of the implements introduced, and permit devices or apparatuses required in the procedure to be introduced into the cavity; these include, for example, implants or catheters intended for embedding within an abdominal tissue or organ to be implanted in the patient. The remaining trocars are used to introduce laparoscopic forceps, other implements, and laparoscopic surgical instruments required for the surgeon to perform the maneuvers undertaken during the operation.

Laparoscopic forceps are among the implements that are of fundamental importance to the successful outcome of a laparoscopic procedure. However, the intra-abdominal manipulation of forceps that are currently available is not always easy. This results in lengthening the duration of the operation, with all the disadvantages and inconveniences such a situation may cause. Extending the time under anesthesia is, of course, detrimental to the patient. Awkwardness in handling surgical instruments within the abdomen may lead to inadvertent injury of adjacent tissues or organs. Additional maneuvers required through a trocar provide additional opportunity for consequential infection from the procedure. In addition, forceps such as those currently available, tend to lose functional effectiveness fairly quickly due to the significant stresses and resulting deformation to which they are subject during the operation. For example, if the implement is a suture needle, the stress, especially stress due to torque, may lead to deformation of the forceps. Furthermore, the forceps do not always have strong grasping power. The grasping power additionally tends to diminish with use due to wear. This may result in potentially harmful changes in position of the implement being grasped, such as a suture needle, particularly when it must be supported and held at a certain angle in relation to the forceps to facilitate suture by the surgeon. When laparoscopic forceps lose their grasping capability, or become deformed, they must be discarded in order to avoid adverse effects on the patient and the procedure. This leads to increased hospital costs.

Forceps that grasp instruments or implements introduced through a trocar during laparoscopic procedures also are frequently called upon to grasp a piece of tissue or a portion of an organ in order to juxtapose the tissue or organ with a laparoscopic implement such as a suture needle. A forceps used to grasp an implement may not always be suitable to grasp a tissue or organ, and vice versa. Such failings lead to a requirement for a multiplicity of laparoscopic forceps to be introduced into the abdominal cavity.

Furthermore, implements currently used in laparoscopic procedures commonly do not have surfaces that are easily grasped without longitudinal or angular slippage. Frequently they may have smooth surfaces and contours that are symmetrical or uniform. Such surfaces are not easily or controllably grasped by a forceps. Implements in question that may fail to be easily grasped or controlled include, for example, laparoscopic suture needles, stylets, devices or implants intended for installation in an abdominal tissue or organ, and the like.

Thus, there remains a need for laparoscopic forceps that have good grasping power and convenient endoscopic maneuverability, thus producing a reduction in the time required to carry out an endoscopic procedure. There furthermore is a need for laparoscopic forceps whose usefulness lasts for an extended amount of time without undergoing deformation under stress. There additionally is a need for a laparoscopic forceps that avoid slippage and twisting of the implement being held. In particular, there remains a need for a forceps that can hold and support a laparoscopic implement such as a suture needle at a particular angle in relation to the shaft of the forceps so as to facilitate its maneuverability by the surgeon. There further remains a need for laparoscopic forceps that are not subject to significant stress during the operation caused, for example, by the torsion of the needle while making the suture stitches.

There further is a need for laparoscopic forceps that permit a laparoscopic implement, such as a needle, when it is grasped, to be automatically oriented in an optimal position for the surgeon to carry out a surgical objective, such as to implant a surgical suture under the guidance of the laparoscopic camera with optimal effectiveness. There is still further a need for laparoscopic forceps that not only grasp and hold an implement, such as a suture needle, in an intended orientation, but that also grasps tissue and organs or can be employed in other maneuvers required during the laparoscopic operation being performed.

The forceps and methods of this invention address and meet such needs. Moreover, the forceps and methods of the present invention eliminate and/or solve the above-mentioned disadvantages of currently existing forceps, particularly as regards known types of laparoendoscopic suture forceps.

SUMMARY OF THE INVENTION

The present invention provides an improved laparoscopic forceps which is matched to a laparoscopic implement so that it can readily grasp the implement, whereby the act of grasping automatically positions the implement in a predetermined and intended orientation. The present invention also provides a method of using the forceps to grasp the implement whereby the act of grasping automatically positions the implement in a predetermined and intended orientation. The forceps are fashioned and/or designed for grasping and automatically orienting the laparoscopic implement in a predetermined and intended orientation. The forceps include a shaft having a first end and a second end, a grasping or gripping mechanism located at the first end of the shaft, a control mechanism located at the second end of the shaft for controlling the grasping mechanism, a communication mechanism passing through the shaft that couples the control mechanism to the grasping mechanism and allows operation of the forceps by a surgeon. The grasping mechanism includes an orienting mechanism effective to orient the implement in a predetermined orientation with respect to the forceps when the grasping mechanism engages the implement. In other embodiments of the forceps, the grasping mechanism includes a plurality of gripping modules or jaws, wherein at least one gripping module is pivotably engaged with the shaft at one of its ends such that it can be induced to pivot by operating the control mechanism. Preferably there are two such gripping modules. They can pivot in unison, gripping or releasing the implement when the control mechanism is operated. Alternatively, one of the gripping modules may be fixed relative to the shaft and the other may pivot.

In still more favorable embodiments of the forceps, the grasping mechanism is effective to orient the implement automatically in the predetermined orientation, and consists of two jaws, each jaw including a flat surface that comes together with and matches with the flat surface of the other jaw. The orienting mechanism implemented by the two jaws includes a recessed seat defined on the flat surface of at least one of the jaws for receiving a portion of the implement. In particular embodiments of the jaw bearing the seat, the seat, being approximately linear, forms an angle less than about 90° with respect to the long axis of the jaw. The angle is preferably between about 10° and about 50°, more preferably is about 30° to about 45°, and even more preferably is about 30°.

In another significant embodiment of the forceps bearing two jaws, a cross section of the seat complements a cross section of the implement in a grip area or zone of the implement and the cross section of the implement in this zone is sufficiently asymmetric that the implement being grasped is oriented with respect to the forceps in the predetermined orientation when the jaws grasp the implement. In still more significant embodiments, the cross section of the seat and the cross section of the zone have approximately circular shapes, and the radius of the seat is at least as large as the radius of the implement. In another advantageous embodiment of the forceps bearing the jaws, the second end of each jaw has knurling, and the surface near the seat is smooth.

In a still additional advantageous embodiment of the forceps, the grasping mechanism is made up of three or more gripping modules each having approximately the same size and shape that are disposed about the shaft at approximately equal angular intervals. When the controlling mechanism is operated, the gripping modules firmly grasp the implement by means of gripping surfaces at their second ends.

Preferably, the laparoscopic forceps and/or the implement to be grasped are specifically designed to mate to each other, whereby the grasping means mates to a specific location or zone on the implement such that, when grasped, the implement is automatically oriented in a specific, predetermined orientation. For example, the specific location or zone on the implement may be approximately linear with a cross section that is sufficiently asymmetric that, when the forceps grasps the implement, the implement automatically rotates or orients about an axis defined along the length of the zone in a predetermined orientation with respect to the forceps. In advantageous embodiments, for example, the cross section of the implement in the zone may be partially circular with at least one flat or non-circular section. The forceps would have a grasping means with a seat to receives the zone, the cross section of the seat having the approximate shape of a portion of a circle such that the partially circular portion of implement will fit within the seat. Still more advantageously, the flat or non-circular section the zone (e.g., a detent having a shoulder at each end and a flat bottom surface) allows the implement to be oriented in a predetermined fashion when grasped by the forceps. The forceps of this invention can be designed and used with a wide range of surgical and other implements.

In still an additional aspect, the invention discloses a method of grasping a laparoscopic implement that has been introduced within the abdominal cavity of a patient undergoing a laparoscopic procedure, whereby the implement is automatically oriented in a predetermined orientation. The forceps and implement to be grasped are designed to have matching and interlocked areas or zones which allows the implement to be automatically oriented when grasped by the forceps. Preferably, the zone to be grasped on the implement has a flat portion having a cross sectional area that is sufficiently asymmetric so that, when the forceps grasps the implement in the zone area, the implement is automatically oriented in a desired and predetermined orientation with respect to the forceps. The forceps employed in the method of the invention may be any of the embodiments of the forceps of the invention that includes grasping mechanisms capable of grasping the implement and orienting it in the predetermined orientation with respect to the forceps. The method includes the steps of (1) introducing the implement through a trocar into the abdominal cavity; (2) introducing at least the first end of the forceps through a trocar into the abdominal cavity; and (3) causing the grasping means of the forceps to grasp the zone of the implement; thereby orienting the implement in the predetermined orientation.

DETAILED DESCRIPTION OF PREFERRED EMBODIMENTS

Figure 1:
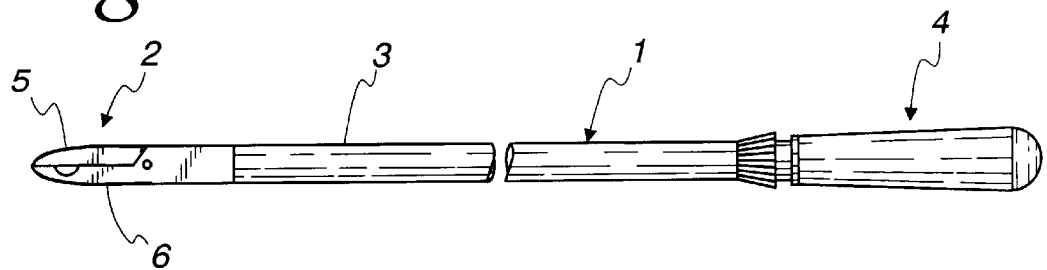
FIG. 1 is a side elevation of the forceps according to the invention.

With reference to FIG. 1, the laparoscopic forceps, indicated by reference number 1, comprise grasping mechanisms 2 located at one end of shaft 3 and control mechanism 4 for controlling the action of the grasping mechanisms 2. The control mechanism communicates with the grasping mechanisms through the shaft. In general, the grasping mechanisms may take the form of any of a variety of gripping modules extending from the end of shaft 3 which, upon activation by the control mechanisms 4, act to grasp or hold a target object. In common applications in laparoscopic surgery, such targets include, by way of nonlimiting example, a laparoscopic implement, device or tool, and portions of tissue or an organ located within the abdomen. The gripping modules include features that permit them, when the target is an implement that is suitably adapted to the gripping modules, to orient the implement in a predetermined orientation with respect to the grasping mechanisms.

Figure 2:
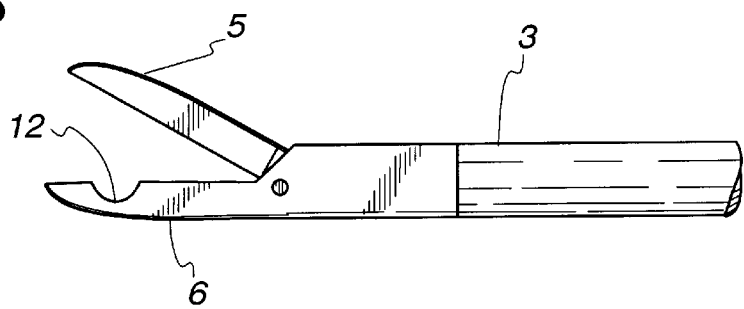
FIGS. 2 and 3 illustrate schematically the forceps of the invention having only one movable jaw, or two movable jaws, respectively.
Figure 3:
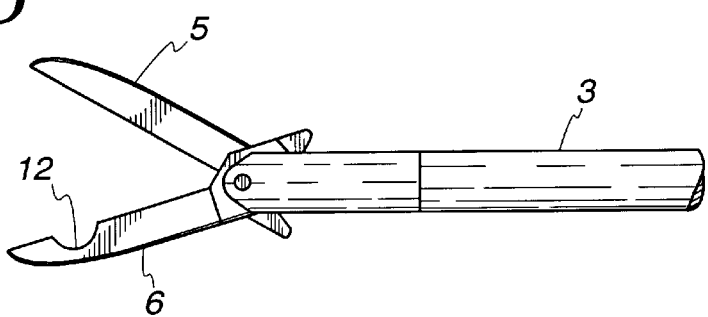

In the embodiment shown in FIG. 1, and amplified further in FIGS. 2, 3, and 6–12, grasping mechanisms 2 comprise gripping modules such as the two jaws 5 and 6 (FIGS. 1–3). At least one of the jaws is moveable, being hingedly or pivotably attached to the shaft 3 at hinge pin 21. FIG. 2 shows an embodiment of the forceps in which one jaw 6 is fixed, and is comprised of a collinear extension of the body of the shaft 3. In this embodiment the moveable jaw 5 may be caused to close down on the fixed jaw 6 in a pivoting motion about the hinge pin 21 upon activation by the control mechanism 4. In a second embodiment, shown in FIG. 3, both jaws 5 and 6 are hingedly or pivotably engaged with the shaft 3 by means of hinge pin 21. In this embodiment the jaws may be closed down on each other in pivoting motion about the hinge pin 21 upon activation by the control mechanism 4.

Figure 4:
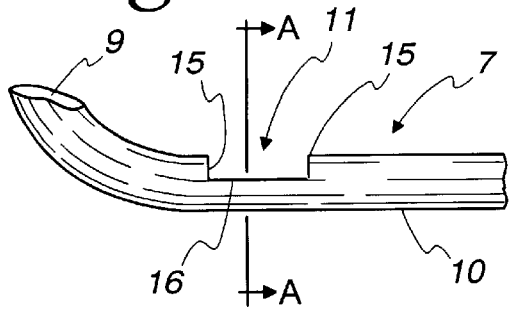
FIG. 4 is a side elevation of a needle or stylet that is to be grasped by the laparoscopic forceps of the invention.

The gripping modules incorporate a mechanism which operates to orient the laparoscopic implement such as a suture needle, a catheter, tunnelling device, or similar device, or as illustrated in FIG. 4, a stylet 7, automatically in an intended way. For example, the jaws 5 and 6 incorporate structural features that permit them to engage with a grip area of the implement to permit the surgeon to maintain and use the implement arrayed in a predetermined orientation with respect to the forceps.

Figure 8:
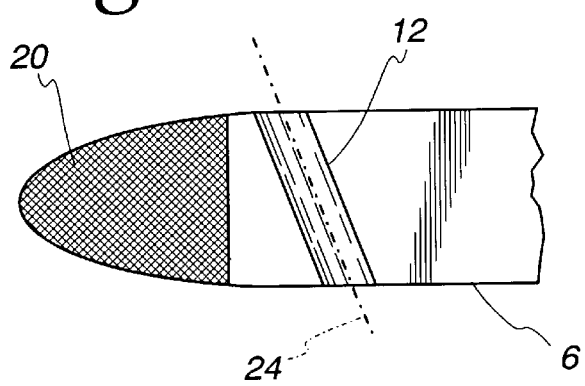
FIGS. 8 and 9 are overhead views of one of the two jaws of the invention, wherein the jaw bears a seat to accommodate an implement.
Figure 9:
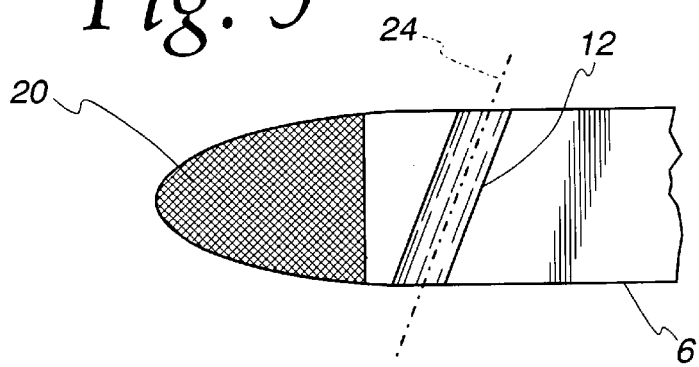

A principal feature of the forceps of the present invention is the presence of a receptacle or seat 12 (FIGS. 2, 3, and 6–12) in at least one of the jaws to accommodate a matched portion of the laparoscopic implement when the jaws are closed on one another. In general, the face of each jaw 5 and 6 includes a flat surface, such as that shown generally at 22 for jaw 6 in FIG. 6, that comes together with and matches with the flat surface of the facing jaw when the controlling mechanism causes the jaw or jaws pivotably to close on one another and grasp an implement located between the jaws. In the embodiment shown in these Figures, especially in FIGS. 6–9, the seat 12 is a groove recessed into jaw 6. In general, the shape of the receptacle is such that it complements the shape of a matching portion on the implement in a region thereof intended to be grasped by the forceps. Since many such implements are essentially linear and cylindrical, the embodiment of the forceps shown in FIGS. 6–9 includes a linear groove 12 recessed into jaw 6 whose cross section is essentially a portion of a circle. The cross sectional view is included at 12 in FIGS. 10–12. The orientation of the receptacle or seat 12 may be defined by identifying a longitudinal axis of the jaw 23 approximately parallel to the shaft 3 of the forceps and a seat axis 24 (FIGS. 8 and 9), and the angle θ formed by the longitudinal axis and the seat axis. Although this angle θ may take on any value, in a preferred embodiment, the angle is less than about 90°, as shown in FIGS. 6–9. More preferably, the angle is between about 10° and about 50°, more preferably, between about 30° and about 40°, and still me preferably about 30°. In FIG. 8 this angle is shown as being an acute angle in an downward orientation; in the mirror image, shown in FIG. 9, the acute angle is in a upward orientation.

In addition, in important embodiments of the forceps the flat surface of each jaw, whether including a seat or receptacle 12, or having no seat, includes a knurled or otherwise roughened surface at the tip, shown at 20, and smooth or polished surfaces at the remainder of the face 22, as well as on the face 22 of the matching surface on the jaw facing the seat, in embodiments in which there is a seat in only one of the jaws. The knurled portion assists in grasping an implement for general purposes (i.e., purposes not directly related to orienting the implement for a particular use) and also assists in grasping a portion of tissue or an organ, when such a grasping is intended. As explained further below, the smooth portion, including a smooth portion that adjoins the receptacle or seat 12, assists in automatically seating an implement being grasped in the intended orientation of the implement. That is, the smooth surfaces permit the implement, such as the stylet or needle, to slide and be inserted into seat 12 with a minimum of frictional resistance. For its part, the implement is preferably smooth in the area or zone to be gripped to promote internal rotation in the seat by the implement, such as the needle or stylet, along its longitudinal axis.

Figure 10:
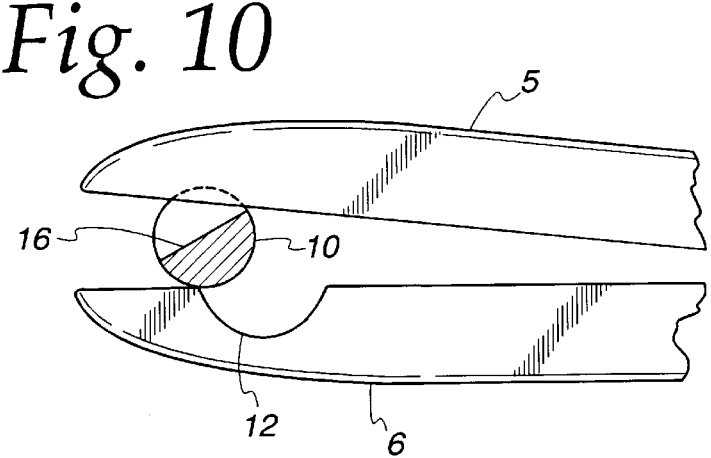
FIGS. 10, 11, and 12 schematically illustrate how an implement, when grasped by the forceps of the invention, is held and automatically oriented to a desired and predetermined orientation or position relative to the forceps.
Figure 11:
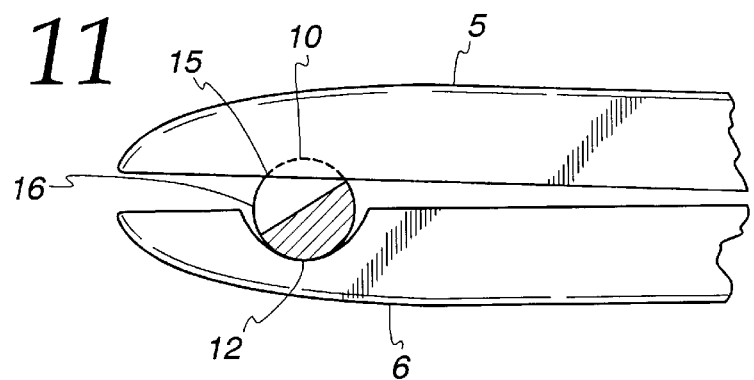
Figure 12:
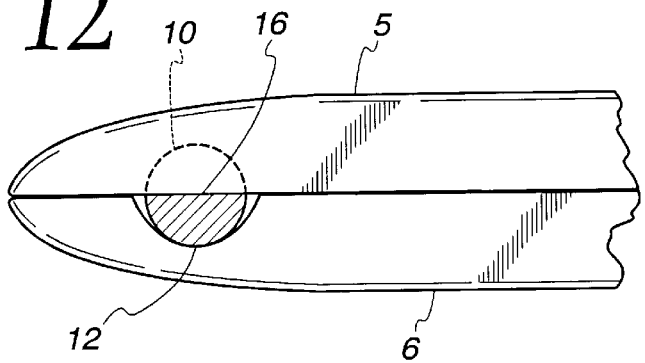

As pointed out above, the shape of seat 12 more or less conforms to, or complements, the shape of the implement to be grasped by the forceps, in a portion of the implement intended to be so held. For example, a portion of an implement (e.g., needle, tunneling device, or stylet) is shown generally at 7 in FIG. 4. It includes a curved smooth noncutting part 8, on whose end is cutting part 9. In the embodiment of such an implement shown in FIG. 4, its cylindrical body 10 includes a portion that is intended to be gripped by the forceps, defined by at least one detent or check 11 with which the forceps engages when the stylet is grasped. In the embodiment of the forceps illustrated in FIGS. 1–3 and 6–12, jaw 5, having no seat therein, engages the detent 11, and jaw 6, bearing a seat, engages the implement by means of the portion, shaded in FIG. 5, that complements the shape of the seat. Check 11, situated in the grip area of the needle, is defined by two shoulders 15 and a bottom surface 16 which is essentially flat. Furthermore, when the cross section of the seat has the approximate shape of a portion of a circle and thus may be described by a radius, and the implement likewise has a cross section that has the approximate shape of at least a portion of a circle with its radius, the radius of the seat is at least as large as the radius of the implement (see especially FIG. 12). As shown best in FIG. 12, the seat 12 may be in the form of a "flattened" half-circle or half-oval so as to allow the implement to easily slip into and fit within the seat. Alternatively, the relative radii of the seat and the grasping zone of the implement may be adjusted so that (as shown in FIGS. 10–12) the implement can easily be rotated when grasped by the forceps so that the implement falls or rolls easily into the seat to orient the implement in a predetermined manner. Furthermore, detent 11 between shoulders 15 balances the stylet, which permits the latter to be positioned, once it has been inserted into the abdomen through the trocar, with the highest possible degree of accuracy.

Figure 5:
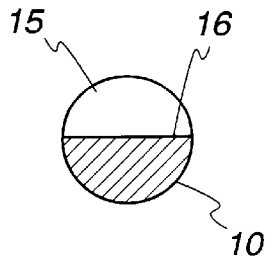
FIG. 5 is a view of the needle or stylet along cross-section line A—A of FIG. 4.
Figure 6:
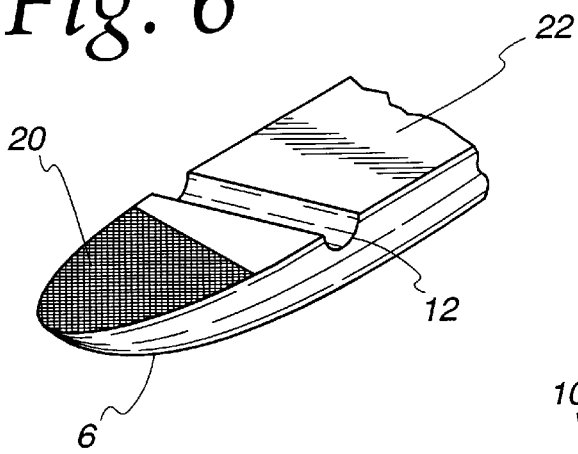
FIG. 6 is a perspective view of the end part of a jaw of the forceps of the invention in which the jaw bears a seat to accommodate an implement.
Figure 7:
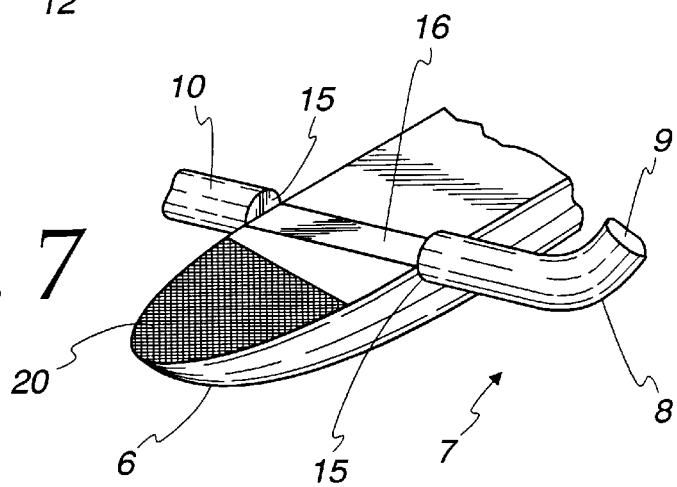
FIG. 7 is a perspective view of the end part of a jaw of the forceps of the invention in which the jaw bears a seat containing a stylet that is to be grasped by the forceps.

A cylinder axis is defined in the cylindrical body 10 of the implement, and the cross section of the implement in this grasped portion is sufficiently asymmetric that the forceps grasps the implement only in such a way that the implement is oriented about the cylinder axis in a unique orientation. Such an asymmetric cross section is illustrated in FIG. 5 for the embodiment of the implement shown in FIG. 4, wherein the asymmetric cross section is the shaded semicircle in the lower portion of FIG. 5. Thus, referring to the perspective view in FIG. 7, if a plane is defined in the implement as containing the cylinder axis and the tip of the cutting part 9, the implement is grasped by the forceps such that the defined plane is oriented about the cylinder axis at a particular rotational angle with respect, for example, to the plane of the jaw surface 22. It is preferred that the longitudinal extent of seat 12 in the jaw and the extent of the detent 11 in the implement be mutually sufficient to permit the entire gripped portion of the implement to be accommodated within the seat once the implement is oriented by closing jaws 5 and 6.

Control mechanisms 4 may be of any type but preferably consist of a constant compression ergonomic caliper handle that is capable of opening and closing the grasping mechanism, such as jaws 5 and 6 of the embodiment in FIGS. 1–3 and 6–12, by means of a kinematic system that is coupled via the shaft.

The operation of the laparoscopic forceps according to the invention is described with reference to FIGS. 10–12. It may be noted that, regardless of whether both jaws 5 and 6 are pivotably moveable or only one of them is, it is possible to introduce a laparoscopic implement such as stylet 7 between them and to cause it to be positioned in seat 12.

The forceps are guided to be opposite the implement in the portion to be grasped, that is, in the zone thereof bearing the check or detent 11. With the jaws opened by the control mechanism, they are maneuvered to engage the portion of the implement to be grasped, such that the flat surface 16 is approximately matched to the jaw not bearing a seat, as shown in FIG. 10. As the surgeon operates the control mechanism to begin closing the jaws, as shown in FIG. 11, the implement is urged by the closing pressure exerted by the jaws to migrate or roll into the seat 12. The pressure, especially of the flat surface of jaw 5 on the bottom surface 16 of the portion of the implement to be grasped, further causes the implement to rotate about its cylindrical axis in a clockwise or counterclockwise direction until the implement is aligned in a predetermined manner within the space from by the seat 12 of jaw 6 and the flat face of jaw 5, thereby permitting the two jaws to close completely, as shown in FIG. 12. In certain embodiments the edges of the detent defined by flat surface 16 and the rest of the body of stylet 7 are, moreover, appropriately rounded in order to facilitate rotation of the stylet on its axis when jaws 5 and 6 are closed. Once jaws 5 and 6 are closed on the stylet, it will be prevented from further rotation and from any lengthwise axial shift in seat 12 by flat surface 16 and the two shoulders 15, respectively. To that end, therefore, the length of the flattened portion 16 is preferably only slightly longer than the length of the seat 12 so that, once gripped by the forceps, the movement of the implement in a longitudinal direction is limited. In this position, for example, when the implement is a stylet, it will always have its tip 9 facing in a predetermined orientation (e.g., in FIG. 7 in an upward direction) for the surgeon, and its positioning in relation to the axis of the laparoscopic forceps will be at a predetermined ideal slant for making suture stitches as required in a surgical procedure.

Figure 13:
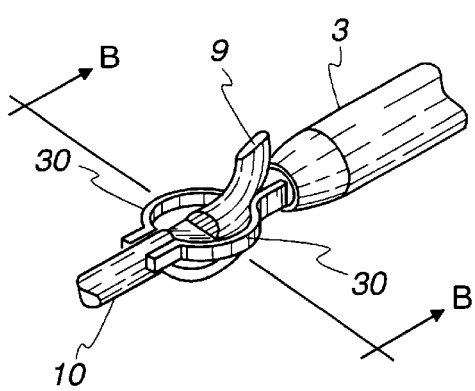
FIG. 13 shows an alternative embodiment of the invention in which three gripping jaws on the laparoscopic forceps grasp a laparoscopic stylet.
Figure 14:
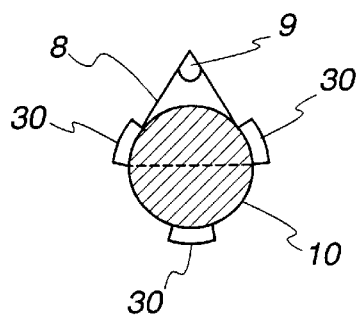
FIG. 14 shows a cross section of the three jaws grasping the implement taken at position B—B of FIG. 13.

An alternative embodiment of the laparoscopic forceps is shown in FIGS. 13 and 14. In this embodiment, the gripping modules used to grasp the laparoscopic implement are at least three jaws 30 that are able to move simultaneously from an open to a closed position and vice versa, in response to the control mechanism. Each jaw is attached to the shaft so that they can be pivoted or moved to open or close the jaws upon the implement. In the embodiment shown in the FIGS. 13 and 14, there are three moving jaws, which are positioned approximately equidistant from one another around the circumference of the center of shaft 3, as may be seen in FIG. 14. As shown in FIG. 13, the jaws grasp an implement such as a stylet, and their size is long enough that each jaw extends beyond tip 9 of the stylet and seizes the stylet on its cylindrical portion, such as shown at 10. Each gripping module has a gripping surface at its second end such that when the control mechanism is operated, the gripping modules firmly grasp the implement by means of the gripping surfaces. The three jaws are additionally mounted such that they are rotatable about the longitudinal axis of the shaft 3, under control of the control mechanism, at the end of the shaft. This permits the surgeon to cause the needle or stylet 7 to rotate on its own cylindrical axis so as to be able to orient it in an intended orientation required by the surgeon. Rotation of the needle on its own axis is needed when, for example, the rotational orientation of the stylet or needle inside the patient's abdomen is not appropriate for the surgeon's needs. The stylet or needle may then be grasped by the a second laparoscopic forceps, such as the embodiment of a forceps described above, since the stylet will have been guided into a favorable orientation and angle to be grasped by such a forceps, thereby permitting suture stitches to be made.

From this mode of operation of the forceps, the advantages of the invention are readily apparent. The stresses to which the stylet will be subject are less intense than that required directly to grasp an object with a symmetrical cross section, and will no longer be transmitted solely to the opening and closing mechanisms of the jaws. Hence the surgeon need exert only fairly light pressure in order to obtain significantly higher holding and grasping power on the stylet. For this reason, moreover, the service life of these laparoscopic forceps is longer than that of traditional laparoscopic forceps. It is evident, furthermore, that, in the unfortunate event that the stylet is incorrectly positioned with the tip pointing down, it is possible to use the accessory laparoscopic forceps with the three moving jaws which are able to grasp the stylet by its central body and rotate it on its axis in order to return it to the ideal position fox the surgeon.

It has been shown in practice that the laparoscopic suture forceps according to the invention are particularly advantageous. Using the forceps of this invention, it is possible to automatically orient, position, and securely hold a laparoscopic stylet, needle, or other surgical implement in an optimal manner according to specific surgical needs by simply grasping and closing the jaws on the forceps. The use of the forceps of the invention allow the avoidance tiresome and complicated movements during laparoscopic surgery. As those skilled in the art will realize, the forceps of this invention can be designed to accommodate the personal preferences of a surgeon and/or for use by left- or right-handed surgeon by, for example, vary the angle between the longitudinal axis of the forceps and the longitudinal axis of the seat (see, for example, FIG. 8 and 9). Moreover, if desired, the implement could have more than one grasping area or zone to allow grasping at different locations along the implement. Moreover, if desired, the forceps could have more than one seat to receive the implement. For example, a forceps could have both the seats shown in FIGS. 8 and 9 (i.e., the seats would intersect) to allow the implement to be grasped in either direction.

The invention so conceived is susceptible to numerous modifications and variants without thereby exceeding the scope of the invention; furthermore, all details may be replaced by technically equivalent elements. In practice, the materials as well as the dimensions used may be of any kind as needed and according to the state of the art.

I claim:

1. Laparoscopic forceps for grasping a laparoscopic implement, said forceps comprising a generally longitudinal shaft having a first end and a second end, a grasping mechanism located at the first end of the shaft, a control mechanism located at the second end of the shaft for controlling the grasping mechanism, and a communication mechanism passing through the shaft that couples the control mechanism to the grasping mechanism so that the grasping mechanism can be opened and closed; wherein the grasping mechanism comprise an orienting mechanism effective to orient the implement in a predetermined orientation when the grasping mechanism engages the implement; wherein the grasping mechanism comprises a first and a second gripping jaws; wherein each of the first and second jaws have a distal and a proximal end wherein the Proximal ends are adjacent to the first end of the shaft; wherein both the first and second gripping jaws are pivotally engaged with the first end of the shaft and can be pivoted by operating the control mechanism such that pivoting the fist and second gripping jaws allows the grasping mechanism to open and close around the implement; wherein each of the first and second jaws comprises a flat surface that matches with the flat surface of the other jaw when the control mechanism causes grasping mechanism to be closed; and wherein the orienting mechanism comprises a recessed seat defined on the flat surface of at least one of the jaws; wherein the recessed seat comprises a receptacle for receiving a portion of the implement and orienting the implement in the predetermined orientation; wherein the first and second jaws, when closed, have a longitudinal axis approximately collinear with the longitudinal axis of the shaft; wherein the recessed seat is essentially linear in shape and is located on and across the flat portion of one of the jaws; wherein a seat axis is defined by the essentially linear recessed seat; and wherein an angle θ formed by the longitudinal axis of the shaft and the seat axis is less than about 90°.

2. The laparoscopic forceps according to claim 4, wherein the angle θ is between about 10° and about 50°.

3. The laparoscopic forceps according to claim 2, wherein the angle θ is between about 30° and about 45°.

4. The laparoscopic forceps according to claim 1, wherein the seat has a cross section that complements a cross section of the implement in a zone of the implement intended to be grasped by the forceps, wherein the zone is approximately linear and has a zone axis, and wherein the cross section of the implement in the zone is sufficiently asymmetric that the forceps grasp the implement in the zone in such a way that the implement is oriented about the zone axis in the predetermined orientation.

5. The laparoscopic forceps according to claim 4, wherein the cross section of the seat has the approximate shape of a portion of a circle and is described by a seat radius, wherein the cross section of the implement in the zone comprises the approximate shape of at least a portion of a circle that is described by an implement radius, and wherein the seat radius is at least as large as the implement radius.

6. The laparoscopic forceps according to claim 1, wherein the flat surfaces at the distal ends of each jaw has knurling or a rough surface and wherein the flat surfaces adjacent to the seat and the proximal ends of jaws are relatively smooth to allow the implement to more easily slide across the flat surfaces and to be seated within the recessed seat in the predetermined orientation.

7. Laparoscopic forceps for grasping a laparoscopic implement, said forceps comprising a generally longitudinal shaft having a first end and a second end, a grasping mechanism located at the first end of the shaft, a control mechanism located at the second end of the shaft for controlling the grasping mechanism, and a communication mechanism passing alone the shaft that couples the control mechanism to the grasping mechanism so that the grasping mechanism can be opened and closed; wherein the grasping mechanism comprise an orienting mechanism effective to orient the implement in a predetermined orientation when the grasping mechanism engages the implement; wherein the grasping mechanism comprises two jaws that can be opened and closed using the control mechanism; wherein the two jaws have essentially flat grasping surfaces; wherein one of the flat grasping surfaces has an essentially linear recessed seat across its flat surface which matches a corresponding area on the implement so that when the corresponding area on the implement is grasped by the grasping mechanism the corresponding area on the implement, the corresponding area on the implement fits within the recessed seat whereby the implement is oriented in a predetermined orientation when the jaws are closed around the implement; wherein the recessed seat has a longitudinal axis which forms an angle θ relative to the shaft's longitudinal axis and wherein the angle θ is less than about 90°.

8. The laparoscopic forceps as defined in claim 7, wherein the angle θ is about 10° to about 50°.

9. The laparoscopic forceps as defined in claim 8, wherein the angle θ is about 30° to about 45°.

10. The laparoscopic forceps as defined in claim 9, wherein the recessed seat has a cross section approximating a semi-circle.

11. Laparoscopic forceps for grasping a laparoscopic implement, said forceps comprising a generally longitudinal shaft having a first end and a second end, a grasping mechanism located at the first end of the shaft, a control mechanism located at the second end of the shaft for controlling the grasping mechanism, and a communication mechanism passing through the shaft that couples the control mechanism to the grasping mechanism so that the grasping mechanism can be opened and closed; wherein the grasping mechanism comprises three or more gripping modules having a first end and a second end and each gripping modules has approximately the same size and shape; wherein the gripping modules are disposed about the shaft at approximately equal angular intervals and wherein each gripping module has a gripping surface it its second end such that, when the controlling mechanism is operated, the gripping modules firmly grasp the implement by means of the gripping surfaces so that the implement can be moved to a desired orientation.

* * * * *

UNITED STATES PATENT AND TRADEMARK OFFICE
CERTIFICATE OF CORRECTION

PATENT NO : 6,146,391
DATED : November 14, 2000
INVENTOR(S): Valerio Cigaina

It is certified that error appears in the above-identified patent and that said Letters Patent are hereby corrected as shown below:

Claim 1, Column 9, Line 33; change "Proximal" to -- proximal --.

Claim 1, Column 9, Line 37; change "fist" to - first -.

Claim 2, Column 9, Line 55; Change "4" to - 1 -.

Claim 7, Column 10, Line 21; Change "alone" to - along -.

Claim 11, Column 10, Line 62; Change "it" to - at -.

Signed and Sealed this

Twenty-ninth Day of May, 2001

Attest:

NICHOLAS P. GODICI

*Attesting Officer*      *Acting Director of the United States Patent and Trademark Office*